(12) United States Patent
Lee et al.

(10) Patent No.: US 8,062,632 B2
(45) Date of Patent: Nov. 22, 2011

(54) SYSTEMS AND METHODS FOR MAKING HEPATOCYTES FROM EXTRAHEPATIC SOMATIC STEM CELLS AND USE THEREOF

(75) Inventors: Oscar Kuang-Sheng Lee, Taipei (TW); Tom Kwang-Chun Kuo, Taipei (TW)

(73) Assignee: National Yang-Ming University, Taipei (TW)

( * ) Notice: Subject to any disclaimer, the term of this patent is extended or adjusted under 35 U.S.C. 154(b) by 186 days.

(21) Appl. No.: 12/489,760

(22) Filed: Jun. 23, 2009

(65) Prior Publication Data

US 2009/0317365 A1    Dec. 24, 2009

Related U.S. Application Data

(60) Provisional application No. 61/074,673, filed on Jun. 23, 2008.

(51) Int. Cl.
*A01N 63/00* (2006.01)
*A01N 65/00* (2009.01)

(52) U.S. Cl. .................. 424/93.1; 435/377; 435/375

(58) Field of Classification Search .................. 424/93.1
See application file for complete search history.

(56) References Cited

OTHER PUBLICATIONS

Liu, J Cell Biochem, 2003, 88:29-40.*
Wagers, 2002, 297:2256-2259.*
Hu, 2010, PNAS, 107:4335-4340.*
Kuo et al., "Stem Cell Therapy for Liver Disease: Parameters Governing the Success of Using Bone Marrow Mesenchymal Stem Cells" Gastroenterology 2008;134:2111-2121.
Banas et al., "Adipose Tissue-Derived Mesenchymal Stem Cells as a Source of Human Hepatocytes" Hepatology 2007; vol. 46, No. 1, 219-228.
Lee et al., "In Vitro Hepatic Differentiation of Human Mesenchymal Stem Cells" Hepatology 2004; vol. 40, No. 6, 1276-1284.
Kang et al., "Fibroblast growth factor-4 and hepatocyte growth factor induce differentiation of human umbilical cord blood-derived mesenchymal stem cells into hepatocytes" World J Gastroenterol 2005;11(47):7461-7465.

* cited by examiner

*Primary Examiner* — Valarie Bertoglio
(74) *Attorney, Agent, or Firm* — Hsiu-Ming Saunders; Intellectual Property Connections, Inc.

(57) ABSTRACT

A method for making hepatocytes from extrahepatic somatic stem cells comprises: a) culturing somatic stem cells in a medium comprising hepatic growth factor to cause the stem cells to differentiate toward hepatocytes; b) culturing cells from a) in a medium comprising HGF and oncostatin M to facilitate the cell differentiation toward hepatocytes; and c) culturing cells from b) in a medium comprising oncostatin M to cause the differentiated cells to mature into hepatocytes, thereby producing a cell population that has morphological features of hepatocytes and at least four of the following characteristics: i) antibody-detectable expression of albumin; ii) real-time reverse transcriptase-polymerase chain reaction-detectable expression of α-fetoprotein, HNF-1α, HNF-3β, HNF-4, HNF-6, α1-antitrypsin, alkaline phosphatase, tryptophan 2,3-dioxygenase, tyrosine aminotransferase, cytochrome P450 family 2 subfamily E polypeptide 1, glutamine synthetase, and/or low density lipoprotein receptor; iii) urea secretion; iv) cytochrome p450 enzyme activity; v) glycogen storage; and vi) low density lipoprotein uptake.

11 Claims, 7 Drawing Sheets

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Forward primer for albumin
```

```
<400> SEQUENCE: 1
aatgttgcca agctgctga                                                 19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for albumin

<400> SEQUENCE: 2
cttcccttca tcccgaagtt                                                20

<210> SEQ ID NO 3
<211> LENGTH: 20
<212> TYPE: DNA
<213> ORGANISM: Artificial Sequence
<220> FEATURE:
<223> OTHER INFORMATION: Forward primer for ALPL

<400> SEQUENCE: 3
agaaccccaa aggcttcttc                                                20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for ALPL

<400> SEQUENCE: 4
cttggctttt ccttcatggt                                                20

<210> SEQ ID NO 5
<211> LENGTH: 20
<212> TYPE: DNA
<213> ORGANISM: Artificial Sequence
<220> FEATURE:
<223> OTHER INFORMATION: Forward primer for TDO2

<400> SEQUENCE: 5
cgatgacagc cttggacttc                                                20

<210> SEQ ID NO 6
<211> LENGTH: 19
<212> TYPE: DNA
<213> ORGANISM: Artificial Sequence
<220> FEATURE:
<223> OTHER INFORMATION: Reverse  primer for TDO2

<400> SEQUENCE: 6
cggaattgca aactctgga                                                 19

<210> SEQ ID NO 7
<211> LENGTH: 20
<212> TYPE: DNA
<213> ORGANISM: Artificial Sequence
<220> FEATURE:
<223> OTHER INFORMATION: Forward primer for TAT

<400> SEQUENCE: 7
ccatgatttc cctgtccatt                                                20

<210> SEQ ID NO 8
<211> LENGTH: 20
<212> TYPE: DNA
```

```
<213> ORGANISM: Artificial Sequence
<220> FEATURE:
<223> OTHER INFORMATION: Reverse primer for TAT

<400> SEQUENCE: 8
ggatggggca tagccattat                                              20

<210> SEQ ID NO 9
<211> LENGTH: 19
<212> TYPE: DNA
<213> ORGANISM: Artificial Sequence
<220> FEATURE:
<223> OTHER INFORMATION: Forward primer for GLUL

<400> SEQUENCE: 9
tctcgcggcc tagctttac                                               19

<210> SEQ ID NO 10
<211> LENGTH: 20
<212> TYPE: DNA
<213> ORGANISM: Artificial Sequence
<220> FEATURE:
<223> OTHER INFORMATION: Reverse primer for GLUL

<400> SEQUENCE: 10
agtgggaact tgctgaggtg                                              20

<210> SEQ ID NO 11
<211> LENGTH: 19
<212> TYPE: DNA
<213> ORGANISM: Artificial Sequence
<220> FEATURE:
<223> OTHER INFORMATION: Forward primer for LDLR

<400> SEQUENCE: 11
ccactcgccc aagtttacc                                               19

<210> SEQ ID NO 12
<211> LENGTH: 18
<212> TYPE: DNA
<213> ORGANISM: Artificial Sequence
<220> FEATURE:
<223> OTHER INFORMATION: Reverse primer for LDLR

<400> SEQUENCE: 12
tgcagcctca gcctctgt                                                18

<210> SEQ ID NO 13
<211> LENGTH: 19
<212> TYPE: DNA
<213> ORGANISM: Artificial Sequence
<220> FEATURE:
<223> OTHER INFORMATION: Forward primer for CYP2E1

<400> SEQUENCE: 13
caagccattt tccacagga                                               19

<210> SEQ ID NO 14
<211> LENGTH: 23
<212> TYPE: DNA
<213> ORGANISM: Artificial Sequence
<220> FEATURE:
<223> OTHER INFORMATION: Reverse primer for CYP2E1

<400> SEQUENCE: 14
caacaaaaga aacaactcca tgc                                          23
```

```
<210> SEQ ID NO 15
<211> LENGTH: 19
<212> TYPE: DNA
<213> ORGANISM: Artificial Sequence
<220> FEATURE:
<223> OTHER INFORMATION: Forward primer for GAPDH

<400> SEQUENCE: 15
agccacatcg ctcagacac                                                19

<210> SEQ ID NO 16
<211> LENGTH: 19
<212> TYPE: DNA
<213> ORGANISM: Artificial Sequence
<220> FEATURE:
<223> OTHER INFORMATION: Reverse primer for GAPDH

<400> SEQUENCE: 16
gcccaatacg accaaatcc                                                19
```

US 8,062,632 B2

SYSTEMS AND METHODS FOR MAKING HEPATOCYTES FROM EXTRAHEPATIC SOMATIC STEM CELLS AND USE THEREOF

REFERENCE TO RELATED APPLICATION

The present application claims the priority to U.S. Provisional Application Ser. No. 61/074,673, filed Jun. 23, 2008, which is herein incorporated by reference in its entirety.

FIELD OF THE INVENTION

The present invention relates generally to hepatocytes, and more specifically to method of making hepatocytes from extrahepatic somatic stem cells.

BACKGROUND OF THE INVENTION

The liver is an extraordinary organ capable of modulating its mass according to functional requirements, proliferating under conditions of functional deficiency, and undergoing apoptosis under functional excess [1]. Upon surgical removal of two-thirds of tissue compensatory growth of the remaining portion is observed in the liver to restore the resected mass, although without anatomical reconstitution [2]. While stem or progenitor cells present in postnatal tissue may contribute to the regeneration of liver, the process takes place without the dependence of such cells. Serial repeated partial hepatectomies performed on rodent liver demonstrated restoration of resected tissue mass in the absence of apparent oval cell proliferation [3]. Further, transplantation of a small number of hepatocytes into urokinase-type plasminogen activator transgenic mice resulted in complete repopulation of the liver [4]. These findings demonstrate that hepatocytes possess proliferative potentials under in vivo environments.

Many patients suffer from liver dysfunctions and diseases and, in the shortage of organ donors, there is an increasing clinical demand for hepatocytes for transplantation-based therapy. Although hepatocytes have been shown to exhibit great replicative capacity in vivo, it has been difficult to obtain primary cultures of hepatocytes that both proliferate and maintain liver-specific functions in vitro [5, 6]. Long-term primary cultures of hepatocytes from various mammalian species have been studied extensively over the past three decades and, while improvements in culture conditions have been made to sustain characteristic hepatic functions, cultured hepatocytes show little replicative capacity in vitro [7-16]. It was not until more recently that Hino et al. and Katsura et al. reported conditions enhancing the in vitro proliferative potential of human hepatocytes while retaining differentiated phenotypes [17, 18]. Nevertheless, it is difficult to obtain large numbers of human hepatocytes for clinical applications.

Somatic stem cells, such as mesenchymal stem cells, are multipotent stein cells capable of differentiating into various lineages of the mesoderm, and are easily accessible from bone marrow, umbilical cord blood, and numerous other postnatal tissues [19-23]. It has been previously demonstrated that somatic stem cells isolated from human bone marrow and umbilical cord blood can differentiate into hepatocyte-like cells with morphology, gene expression, and in vitro functions characteristic of hepatocytes [20, 24, 25]. Albeit the differentiated cells exhibit a number of hepatic characteristics, these cells do not possess and sustain a complete repertoire of the properties of parenchymal liver cells, indicating that the differentiation process is only partial.

A previously unaddressed need exists in the art to address the aforementioned deficiencies and inadequacies, especially in connections with culturing hepatocytes.

SUMMARY OF THE INVENTION

In one aspect, the invention relates to a method for preparing hepatocytes. comprising the steps of: a) culturing extrahepatic somatic stem cells in a medium comprising hepatic growth factor (HGF) to cause the somatic stem cells to differentiate toward hepatocytes; b) culturing cells from a) in a medium comprising HGF and oncostatin M (OSM) to facilitate the process of cell differentiation toward hepatocytes; and then c) culturing cells from b) in a medium comprising OSM to cause the differentiated cells to mature into hepatocytes, thereby producing a cell population that has the morphological features of hepatocytes and at least four of the following characteristics: i) antibody-detectable expression of albumin; ii) Real-time reverse transcriptase-polymerase chain reaction-detectable expression of α-fetoprotein, HNF-1α, HNF-3β, HNF-4, HNF-6, α1-antitrypsin, alkaline phosphatase, tryptophan 2,3-dioxygenase, tyrosine aminotransferase, cytochrome P450 family 2 subfamily E polypeptide 1, glutamine synthetase, and/or low density lipoprotein receptor; iii) evidence of urea secretion; iv) evidence of cytochrome p450 enzyme activity; v) evidence of glycogen storage; and vi) evidence of uptake of low density lipoprotein.

In one embodiment of the invention, the aforementioned step a) comprises culturing extrahepatic somatic stem cells in a medium comprising HGF, fibroblast growth factor-2 (FGF-2) and fibroblast growth factor-4 (FGF4).

In another embodiment of the invention, the aforementioned step b) comprises culturing cells in a medium comprising OSM, HGF, FGF-2, FGF-4 and a bone morphogenic protein (BMP).

In another embodiment of the invention, the BMP is at least one selected from the group consisting of BMP2, BMP3, BMP4, BMP6, BMP7 and BMP8a.

In another embodiment of the invention, the BMP is replaced with a composition comprising nicotinamide, ascorbic acid, insulin, human transferrin and selenous acid.

Further in another embodiment of the invention, the step c) comprises culturing cells in a medium comprising OSM, HGF, FGF-1, FGF-2, FGF-4, dexamethasone, insulin, human transferrin, selenous acid, nicotinamide and ascorbic acid.

Yet in one embodiment of the invention, the culturing in step a) is for a period of at least about 4 days, the culturing in step b) is for a period of about from one to five days, and the culturing in step c) is for a period of at least about 9 days.

In another aspect, the invention relates to a method for preparing hepatocytes comprising the steps of: a) culturing extrahepatic somatic stem cells in a medium comprising HGF, fibroblast growth factor-2 (FGF-2) and fibroblast growth factor4 (FGF-4); b) culturing cells from a) in a medium comprising OSM, HGF, FGF-2, FGF4 and a bone morphogenic protein (BMP); and then c) culturing cells from b) in a medium comprising OSM, HGF, FGF-1, FGF-2, FGF-4, dexamethasone, insulin, human transferrin, selenous acid, nicotinamide and ascorbic acid, thereby producing hepatocytes.

Further in another aspect, the invention relates to isolated hepatocytes prepared according to one of the aforementioned methods.

Further in another aspect, the invention relates to a method for promoting and/or restoring liver function in an animal in need thereof comprising the step of administering to the animal an effective amount of the aforementioned hepatocytes.

Yet in another aspect, the invention relates to a method for identifying a compound that affects the expression of a hepatic cell marker comprising the steps of: a) exposing the aforementioned hepatocytes to a test compound; b) detecting the expression level of the hepatic cell marker in the hepatocytes exposed to the test compound; and c) comparing the expression level of the hepatic cell marker in the hepatocytes exposed to the test compound with the expression level of the hepatic cell marker in the hepatocytes not exposed to the test compound to determine whether the test compound affects the expression of the hepatic cell marker.

The hepatic cell marker may be selected form the group consisting of albumin, α-fetoprotein, HNF-1α, HNF-3β, HNF-4, HNF-6, α1-antitrypsin, alkaline phosphatase, tryptophan 2,3-dioxygenase, tyrosine aminotransferase, cytochrome P450 family 2 subfamily E polypeptide 1, glutamine synthetase, low density lipoprotein receptor, urea secretion, glycogen storage, and low density lipoprotein uptake.

In another aspect, the invention relates to a method for identifying a compound that affects the expression of a hepatic cell marker comprising the steps: a) exposing the aforementioned hepatocytes to a test compound; b) detecting the expression level of the hepatic cell marker in the hepatocytes exposed to the test compound; and c) comparing the expression level of the hepatic cell marker in the hepatocytes exposed to the test compound with that in the hepatocytes not exposed to the test compound to determine whether the test compound affects the expression of the hepatic cell marker.

Further in another aspect, the invention relates to a method for identifying a compound that affects liver function comprising the steps: a) exposing the aforementioned hepatocytes to a test compound; b) detecting the level of urea secretion, cytochrome p450 enzyme activity and/or uptake of low density lipoprotein of the hepatocytes exposed to the test compound; and c) comparing the level of urea secretion, cytochrome p450 enzyme activity and/or uptake of low density lipoprotein of the hepatocytes exposed to the test compound with that of the hepatocytes not exposed to the test compound to determine whether the test compound affects a liver function.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figures 1A, 1C:
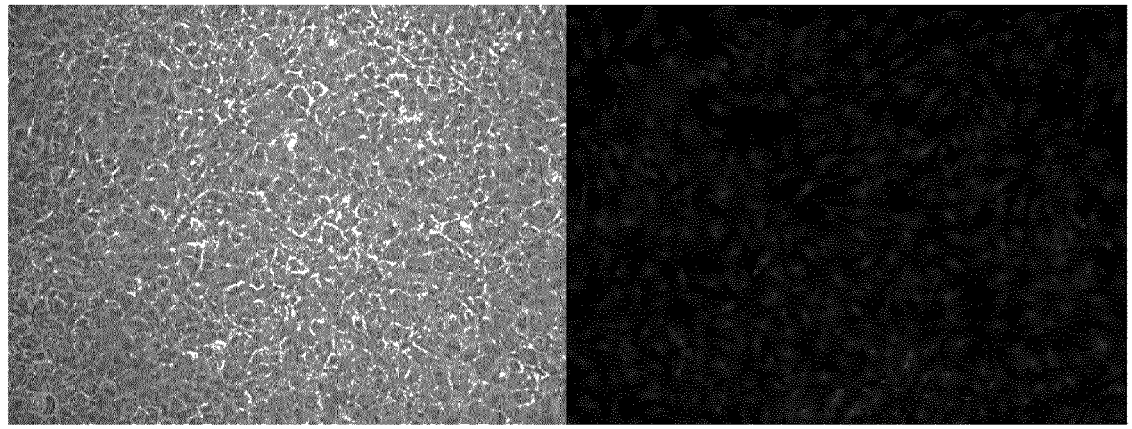
FIG. 1A shows the morphology of hepatocytes differentiated from somatic stem cells cultured under hepatogenic conditions.
FIG. 1C shows the results of immunostaining for albumin in hepatocytes differentiated from somatic stem cells cultured under hepatogenic conditions.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "somatic stem cell," shall generally mean multipotent stem cells that can differentiate into a variety of cell types. Cell types that somatic stem cells have been shown to differentiate into in vitro or in vivo include osteoblasts, chondrocytes, myocytes, adipocytes, and beta-pancreatic islets cells. The term somatic stem cells can encompass multipotent cells derived from other non-marrow tissues, such as adult muscle side-population cells or the Wharton's jelly present in the umbilical cord, adipose tissue, as well as in the dental pulp of deciduous baby teeth. Because somatic stem cells yet do not have the capacity to reconstitute an entire organ, the term "multipotent stromal cell" has been proposed as a better replacement.

As used herein, "extrahepatic somatic stem cell" shall generally mean any type of somatic stem cells derived from tissues other than the liver, e.g., muscle-derived stem cells, adipose-derived stem cells, placenta-derived stem cells, umbilical cord/umbilical cord-blood-derived stem cells, menstrual blood-derived stem cells, etc.

As used herein, "ITS+Premix" is a universal culture supplement which contains insulin, human transferrin, and selenous acid, the three most universally essential components of defined culture media. They stimulate cell proliferation of a variety of cells under serum-reduced conditions.

The full names for abbreviations used herein are as follows: ALPL for alkaline phosphatase, TDO2 for tryptophan 2,3-dioxygenase, TAT for tyrosine aminotransferase, GLUL for glutamine synthetase, LDLR for low density lipoprotein receptor, CYP2E1 for cytochrome P450 family 2 subfamily E polypeptide 1.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Materials and Methods

Isolation of human somatic stem cells. Human bone marrow was aspirated from the femur of healthy donors during fracture surgery with informed consent. Total mononuclear cells were obtained by negative immuno-depletion of CD3, CD14, CD19, CD38, CD66b, and glycophorin-A positive cells using antibodies (RosetteSep®, StemCell Technologies, Vancouver, BC, Canada), followed by Ficoll-Paque (Amersham-Pharmacia, Piscataway, N.J., USA) density gradient centrifugation (1.077 g/cm$^3$), and plated in tissue culture flasks (Becton Dickinson, Franklin Lakes, N.J., USA) with Iscove's modified Dulbecco's medium (IMDM, Gibco BRL, Grand Island, N.Y., USA) and 10% Fetal Bovine Serum (FBS, Hyclone, Logan, Utah, USA) supplemented with 10 ng/ml epidermal growth factor (EGF; R&D Systems, Minneapolis, Minn., USA), 10 ng/ml fibroblast growth factor-2 (FGF-2; R&D Systems), 100 U penicillin, 1000 U streptomycin, and 2 mM L-glutamine (Gibco BRL). Non-adherent cells were removed by medium changes at 12-18 hours post plating. Adherent cells were cultured and colonies that developed from the culture were transferred into new vessels and culture expanded under the same conditions. Cells that showed proliferative advantage were collected and were regarded as stem cells.

Generation of hepatocytes from extrahepatic somatic stem cells. To generate hepatocytes from extrahepatic somatic stem cells, stem cells were seeded at about $1.7 \times 10^4$ cells/cm$^2$ and treated sequentially with the following media: Day 0-7: L-15 Medium supplemented with 20 ng/ml hepatocyte growth factor (HGF; R&D Systems), 10 ng/ml FGF-2 (R&D Systems), and 10 ng/ml FGF-4 (R&D Systems). Day 8-12: L-15 medium supplemented with 5 ng/ml FGF-2, 5 ng/ml FGF4, 10 ng/ml HGF, 10 ng/ml oncostatim M (OSM; R&D Systems), 10 mM nicotinainide (Sigma-Aldrich), 1 mM ascorbic acid (Sigma-Aldrich), and 1% (v/v) ITS+ premix supplement (Becton-Dickinson). Day 13-28: L-15 medium supplemented with 1 ng/ml FGF-2, 1 ng/ml FGF-4, 2 ng/ml HGF, 20 ng/ml OSM, 10 mM nicotinamide, 1 mM ascorbic acid, $10^{-6}$ M dexamethasone, and 1% (v/v) ITS+ premix supplement.

Total RNA isolation and reverse transcriptase-polymerase chain reaction (RT-PCR). Total RNA was prepared from cells using RNEasy kit (Qiagen, Stanford, Valencia, Calif., USA). The first strand cDNA was synthesized using Advantage RT-for-PCR kit (Clontech, Palo Alto, Calif., USA). cDNA was amplified by PCR using Eppendorf MasterCycler Gradient (Eppendorf, Hamburg, Germany). The PCR profile was an initial cycle of 5 min at 94° C., followed by 36 cycles of 30 sec at 94° C., 30 sec at 60° C., and 40 sec at 72° C., and a final cycle of 5 min at 72° C.

Immunocytochemistry. To investigate the formation of hepatocytes from stem cells, somatic stem cells and hepatocytes differentiated therefrom were assessed for the production of albumin, which is a function specific to hepatocytes. Briefly, cells growing on 4-well-chamber slides (Becton Dickinson) at about $1.0\text{-}1.7 \times 10^4$ cells/cm$^2$ were fixed in 4% formaldehyde and permeabilized with 0.1% Triton X-100 (Sigma-Aldrich) for 10 minutes. Samples were washed 3 times with blocking solution (phosphate buffered saline (PBS), 5% normal goat serum) each for 5 minutes and incubated with mouse IgG primary antibody (anti-human albumin, Sigma-Aldrich, 1:50; anti-cytokeratin-18, Sigma-Aldrich, 1:50) for 16-20 hours at 4° C. Samples were washed 3 times in PBS each for 5 minutes and incubated with Cy3-conjugated goat anti-mouse IgG secondary antibody (Sigma-Aldrich, 1:100) for 1 hour at room temperature, then washed 3 times in PBS each for 5 minutes. Staining results were visualized with an epifluorescence microscope and images were taken using a SPOT RT imaging system (Diagnostic Instruments, Sterling Heights, Mich., USA).

Uptake of Low-Density Lipoprotein (LDL). Normal hepatocytes are capable of LDL uptake. The ability to take up LDL is therefore an indicator of stem cell-differentiated hepatocytes. Undifferentiated stem cells and stem cell-differentiated hepatocytes growing on 4-well chamber slides (Becton Dickinson) at about $1.0-1.7 \times 10^4$ cells/cm$^2$ were incubated with fluorochrome-conjugated LDL (Dil-Ac-LDL; Biomedical Technologies, Stoughton, Mass., USA) for 4-8 hours at 37° C., 5% $CO_2$, which enables the detection of LDL-uptake by cells with an epifluorescence microscope. Imaging was preformed using SPOT RT imaging system.

Pentoxyresorufin-O-deakylase (PROD) assay. Pentoxyresorufin is dealkylated by cytochrome P450 to resorufin, which emits a red fluorescence signal upon excitation with an epifluorescence microscope. The presence of this activity denotes that stem cells are well differentiated into hepatocytes, which have drug-metabolizing enzymes. The assay was performed as follows: Briefly, undifferentiated somatic stem cells and differentiated hepatocytes growing on 4-well chamber slides (Becton Dickinson) at about $1.0-1.7 \times 10^4$ cells/cm$^2$ were stimulated with 1 mM phenobarbital in culture media for 72 hours and then treated with 10 µM pentoxyresorufin. The cytochrome P450 enzyme activity was examined with an epifluorescence microscope. Imaging was performed using SPOT RT imaging system.

Results

Figure 1B:
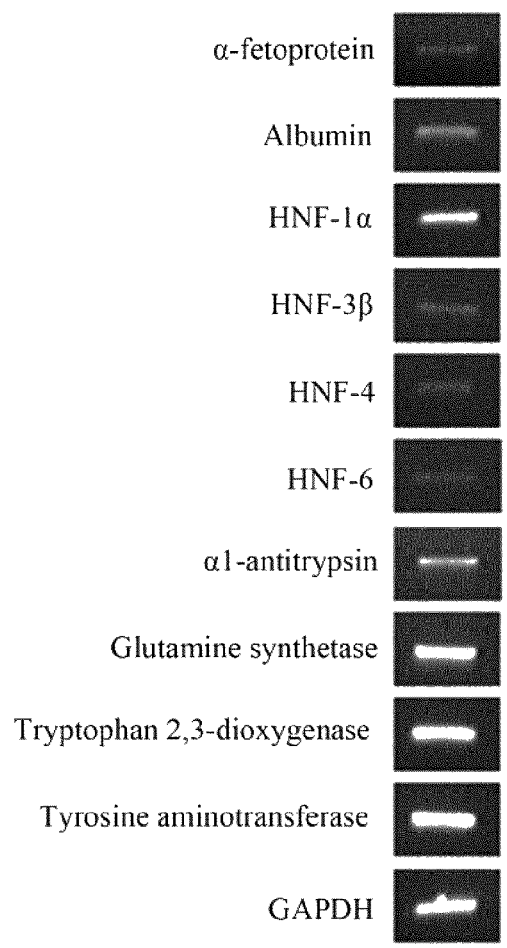
FIG. 1B shows the expressions of various liver marker genes in hepatocytes differentiated from somatic stem cells cultured under hepatogenic conditions.

Differentiation of Somatic stem cells into functional hepatocytes. Somatic stem cells treated sequentially with different factors under the aforementioned conditions differentiated into cells that manifested phenotypic characteristics of hepatocytes. FIG. 1A shows hepatocyte-like cells differentiated from somatic stem cells cultured under hepatogenic conditions. These differentiated cells exhibited polygonal morphologies characteristic of hepatocytes. They were further characterized by the expression of a comprehensive panel of liver marker genes such as α-fetoprotein, albumin, hepatocytes nuclear factor-1α (HNF-1α), hepatocytes nuclear factor 3β (HNF-3β), hepatocytes nuclear factor 4 (HNF-4), hepatocytes nuclear factor 6 (HNF-6), α1-antitrypsin, glutamine synthetase, tryptophan 2,3-dioxygenase and tyrosine aminotransferase (FIG. 1B). GAPDH serves as house-keeping gene. The expressions of these genes suggest that stem cells have become hepatocytes under the hepatogenic conditions.

Figures 1D, 1E:
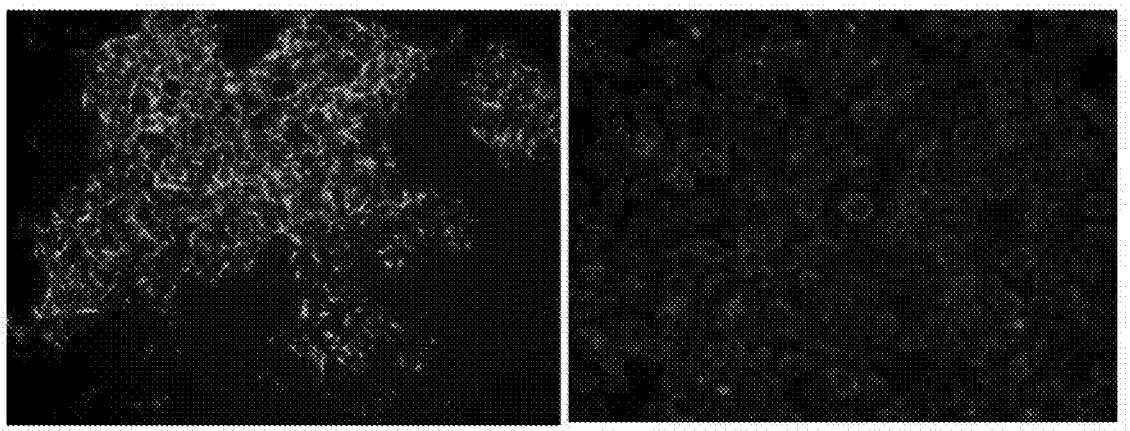
FIG. 1D shows the results of immunostaining for cytokeratin-18 in hepatocytes differentiated from somatic stem cells cultured under hepatogenic conditions.
FIG. 1E shows the results of assay for low density lipoprotein uptake in hepatocytes differentiated from somatic stem cells cultured under hepatogenic conditions.
Figures 1F, 1G:
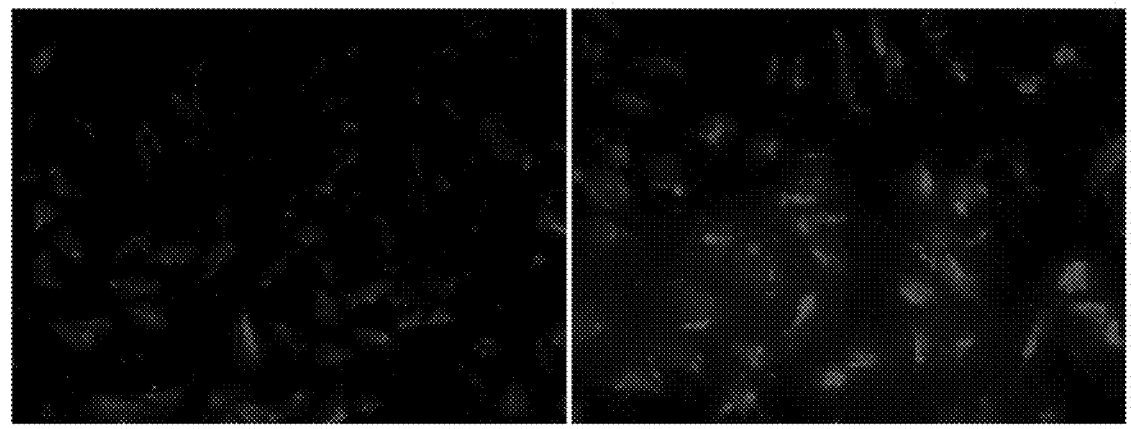
FIG. 1F shows the results of the detection of cytochrome P450 enzymatic activity in hepatocytes differentiated from somatic stem cells cultured under hepatogenic conditions in the absence of Phenobarbital.
FIG. 1G shows the results of the detection of cytochrome P450 enzymatic activity in hepatocytes differentiated from somatic stem cells cultured under hepatogenic conditions in the presence of phenobarbital stimulation.

To further confirm the hepatic phenotype of stem cell-differentiated hepatocytes, a number of assays were performed to assess the functions of differentiated cells. Somatic stem cell-differentiated hepatocytes were stained positive for albumin (FIG. 1C). These somatic stem cell-differentiated hepatocytes were also stained positive for cytokeratin-18, a liver filament protein (FIG. 1D). The results of the LDL-uptake as determined by epifluorescence microscopy indicated that the somatic stem cell-differentiated hepatocytes exhibited the ability to take up fluorochrome-conjugated LDL (FIG. 1E). These somatic stem cell-differentiated hepatocytes exhibited cytochrome P450 enzyme activity, i.e., the ability to convert pentoxyresorufin into resorufin, as shown under the epifluorescence microscopy (FIG. 1F). Resorufin produces a red fluorescence upon excitation. The cytochrome P450 enzyme activity in the somatic stem cell-differentiated hepatocytes could be stimulated by Phenobarbital (FIG. 1G). Taken together, these results demonstrate that stem cells cultured under hepatogenic conditions acquire phenotypic and functional characteristics of hepatocytes.

Many patients suffer from metabolic liver diseases such as haemochromatosis, Wilson disease, $\alpha_1$-antitrypsin deficiency, glycogen storage disease, hereditary tyrosinaemia type I, chronic hepatitis, liver cirrhosis, and cystic fibrosis, as well as acute liver failures resulting from viral, drug, toxin, or immune-mediated insults. In most cases, liver transplantation is currently the only effective treatment for these patients, but the availability of donor organs for clinical use is very limited. For those suffering from acute liver failures, patients often die before an appropriate organ is available [26]. Fortunately, many of the disorders treated by liver transplantation are diseases caused by hepatocyte dysfunction and are unnecessary to replace the entire organ, and could potentially be overcome by hepatocyte transplantation [27]. For this reason, extensive efforts have been devoted to exploring the use of cell transplantation as an alternative to the entire organ and, although limited, some success has been reported [4, 28, 29].

Although normal hepatocytes may serve as an alternative to organ transplantation, the availability of large quantities of cells for clinical use remains to be a problem, and efforts are ongoing in the search for alternative sources for cell transplantation. In contrast to normal hepatocytes, somatic stem cells are readily accessible from the bone marrow, and have also been shown to be isolatable from trabecular bone, synovial membrane, lipoaspirates and umbilical cord blood [19-23]. The ability of somatic stem cells to be propagated prior to and following hepatic differentiation could potentially overcome the shortage of cells for transplantation and provide functional support for patients suffering from liver failure and thus making it an ideal candidate in the clinical setting. In addition, the ability to differentiate somatic stem cells into mature hepatocytes functionally equivalent to those derived from the liver suggest potential applications in drug screening and pharmacological studies as exemplified by the ability to metabolize pentoxyresorufin into resorufin.

Example 2

Materials and Methods

Generation of hepatocytes from extrahepatic somatic stem cells. Extrahepatic somatic stem cells were first isolated according to the procedures as aforementioned. To generate hepatocytes from the extrahepatic somatic stem cells, stem cells were seeded at about $1.7 \times 10^4$ cells/cm$^2$ and treated sequentially with the following media: Day 0-9: DMEM/F12 supplemented with 20 ng/ml hepatocyte growth factor (HGF; R&D Systems), 10 ng/ml FGF-2 (R&D Systems), 10 ng/ml FGF-4 (R&D Systems). Day 9-12: DMEM/F12 supplemented with 20 ng/ml oncostatin M (OSM; R&D Systems), 20 ng/ml HGF, 2 ng/ml FGF-2, 2 ng/ml FGF4, 10 ng/ml bone morphogenetic protein 2 (BMP-2; R&D Systems). Day 12-28: DMEM/F12 supplemented with 20 ng/ml OSM, 1 ng/ml HGF, 0.1 ng/ml FGF-1, 0.1 ng/ml FGF-2, 0.1 ng/ml FGF-4, $10^{-6}$ M dexamethasone (Sigma-Aldrich), 1×ITS+ premix supplement (Becton-Dickinson), 0.61 g/L nicotinamide (Sigma-Aldrich), 200 mM ascorbic acid (Sigma-Aldrich). Media changes were performed at 3-day intervals.

Real-time reverse transcriptase-polymerase chain reaction. To investigate the formation of hepatocytes from somatic stem cells, expression of numerous marker genes that are characteristic of mature hepatocytes were investigated: albumin (ALB), alkaline phosphatase (ALPL), tryptophan 2,3-dioxygenase (TDO2), tyrosine aminotransferase (TAT), glutamine synthetase (GLUL), low density lipoprotein receptor (LDLR) and cytochrome P450, family 2, subfamily E, polypeptide 1 (CYP2E1). Total RNA was prepared from cells using RNEasy kit (Qiagen, Stanford, Valencia, Calif., USA). First strand cDNA was synthesized using Advantage RT-for-PCR kit (Clontech, Palo Alto, Calif., USA). For detection of genes expression by real-time PCR, the first strand cDNA (300 ng) was diluted in a 10 μl reaction containing 2×PCR MasterMix reagent, 200 nM each of sense and anti-sense primers, 100 nM of Universal ProbeLibrary probe. The reactions were incubated in a LightCycler 480 (Roche) at 95° C. for 10 minutes, 40 cycles of 95° C. for 10 seconds followed by 60° C. for 1 minute, and finally 40° C. for 10 seconds. Primers used for real time PCR detection of liver marker genes are shown in Table 1.

TABLE 1

| Gene | Forward primer | SEQ ID NO. | Reverse primer | SEQ ID NO. |
|---|---|---|---|---|
| ALB | aatgttgccaagctgctga | 1 | cttcccttcatcccgaagtt | 2 |
| ALPL | agaacccaaaggcttcttc | 3 | cttggcttttccttcatggt | 4 |
| TDO2 | cgatgacagccttggacttc | 5 | cggaattgcaaactctgga | 6 |
| TAT | ccatgatttccctgtccatt | 7 | ggatggggcatagccattat | 8 |
| GLUL | tctcgcggcctagctttac | 9 | agtgggaacttgctgaggtg | 10 |
| LDLR | ccactcgcccaagtttacc | 11 | tgcagcctcagcctctgt | 12 |
| CYP2E1 | caagccattttccacagga | 13 | caacaaaagaaacaactccatgc | 14 |
| GAPDH | agccacatcgctcagacac | 15 | gcccaatacgaccaaatcc | 16 |

Immunocytochemistry. To investigate the formation of hepatocytes from somatic stem cells, cells were assessed for the production of albumin. Cells growing on 4-well chamber slides (Becton Dickinson) at about $1.0\text{-}1.7\times10^4$ cells/cm$^2$ were fixed in 4% formaldehyde, and permeabilized with 0.1% Triton X-100 (Sigma-Aldrich) for 10 minutes. Samples were washed 3 times, each for 5 minutes, with blocking solution (phosphate buffered saline (PBS), 5% normal goat serum) and incubated with mouse IgG anti-human albumin antibody (Sigma-Aldrich, 1:50) for 16-20 hours at 4° C. Samples were washed 3 times in PBS, each for 5 minutes, and incubated with Cy3-conjugated goat anti-mouse IgG secondary antibody (Sigma-Aldrich, 1:100) for 1 hour at room temperature, then washed 3 times in PBS, each for 5 minutes. Staining results were visualized with an epifluorescence microscope and imaging was performed with SPOT RT imaging system (Diagnostic Instruments, Sterling Heights, Mich., USA).

Low-density lipoprotein (LDL) uptake. The ability of somatic stem cell-differentiated hepatocyes to take up LDL was examined according to the aforementioned method.

Urea secretion. The ability of somatic stem cell-differentiated hepatocytes to secrete urea was investigated because urea secretion is a function characteristic of normal hepatocytes. Culture media were collected from cultures of undifferentiated stem cells and from stem cell-differentiated hepatocytes. Urea concentrations were determined by the QuantiChrome urea assay kit (BioAssay Systems, Hayward, Calif., USA) and analyzed with a Bio-Rad Model 680 microplate reader (Hercules, Calif., USA).

Pentoxyresorufin-O-dealkylase (PROD) assay. The activity of pentoxyresorufin-O-dealkylase was assayed to investigate the ability of somatic stem cell-differentiated hepatocytes to metabolize drugs according to the procedure as aforementioned.

Periodic acid-Schiff (PAS) for glycogen. The ability to store glycogen is a function characteristic of normal hepatocytes. Thus, glycogen storage in the somatic stem cell-differentiated hepatocytes was examined on undifferentiated somatic stem cells and somatic stem cell-differentiated hepatocytes. Cells growing on 4-well chamber slides (Becton Dickinson) at about $1.0\text{-}1.7\times10^4$ cells/cm$^2$ were fixed in 4% formaldehyde, permeabilized with 0.1% Triton X-100 for 10 minutes. The cells were then oxidized in 1% periodic acid for 5 minutes, rinsed 3 times in dH$_2$O, treated with Schiff's reagent for 15 minutes and rinsed in dH$_2$O for 5-10 minutes.

Rescue of fulminant hepatic failure. An animal model of acute liver failure was used to evaluate the capability of stem cell-differentiated hepatocytes to rescue recipient animals from liver failure. To avoid rejection of human cells when transplanted into mice, non-obese diabetic severe combined immunodeficient (NOD-SCID) mice were used. NOD-SCID mice were purchased from Tzu Chi University Laboratory Animal Center (Hualien, Taiwan). All animal experiments were performed with the approval of the Animal Care Committee. To induce fulminant hepatic failure in NOD-SCID mice, carbon tetrachloride (CCl$_4$) was dissolved in mineral oil at 10% concentration and administered to animals by gavage at a dosage of 0.28 ml CCl$_4$/kg body weight. This led to submassive necrosis of the liver and resulted in 100% lethality in recipient animals by day-6 after administration of CCl$_4$. To test the ability of stem cell-differentiated hepatocytes to rescue recipient animals, transplantation of $4.2\times10^7$/kg stem cell-differentiated hepatocytes was performed at 24 hours post administration of CCl$_4$ under 3% isoflurane inhalation anesthesia. Control animals were transplanted with PBS as placebo.

Histological and immuno-histological analysis. To assess the extent of liver damage induced by the administration of CCl$_4$ as well as the extent of regeneration after cell transplantation, mice were sacrificed at 4 weeks post administration of CCl$_4$ and liver tissue were excised from NOD-SCID mice (both placebo and cell-transplant group) for sectioning and staining. Tissues were fixed in 3.7% formaldehyde, dehydrated, embedded in paraffin blocks and sectioned at 3-4 μm. For histology, sections were stained with Hematoxylin and Eosin (Sigma-Aldrich). To further investigate the engraftment and functionality of transplanted cells in the liver of recipient animals, liver sections were assessed for the presence of human albumin produced by the transplanted cells. Sections were blocked with blocking solution and incubated with mouse IgG anti-human albumin antibody (Sigma-Aldrich, 1:50) for 16-20 hours at 4° C. Samples were washed 3 times in PBS, each for 5 minutes, and incubated with Cy3-conjugated goat anti-mouse IgG secondary antibody (Sigma- Aldrich, 1:100) for 1 hour at room temperature, then washed 3 times in PBS, each for 5 minutes. Staining results were visualized with an epifluorescence microscope and imaging was performed with SPOT RT imaging system.

Results

Figure 2A:
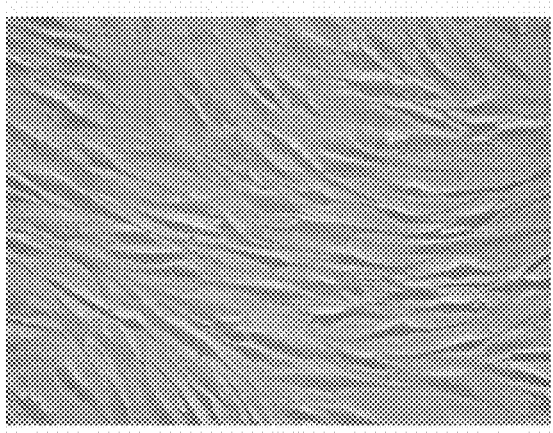
FIG. 2 shows the morphology of bone marrow-derived stem cells cultured under (A) stem cell maintenance conditions, and (B) after treatment with the first hepatogenic medium, (C) after treatment with the second hepatogenic medium, and (D) after treatment with the third hepatogenic medium.
Figure 2B:
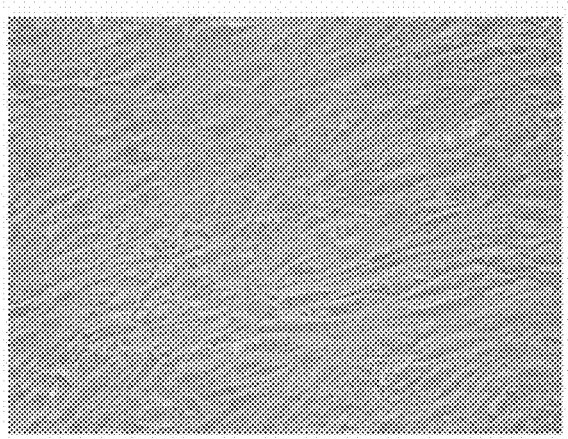
Figure 2C:
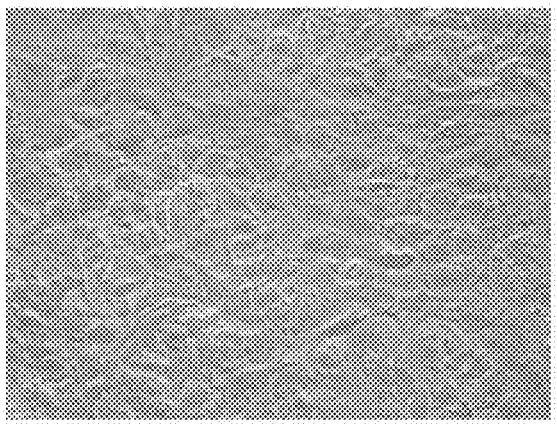
Figure 2D:
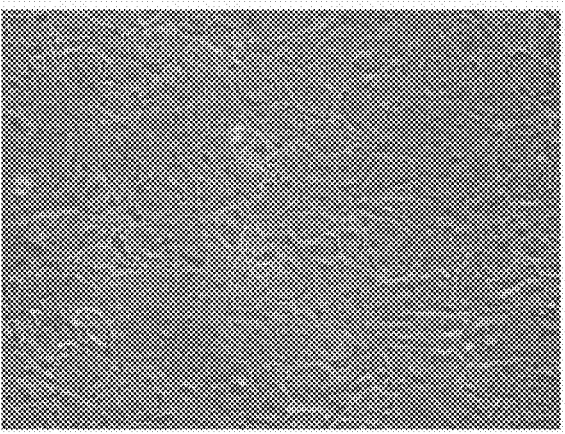
Figure 3A:
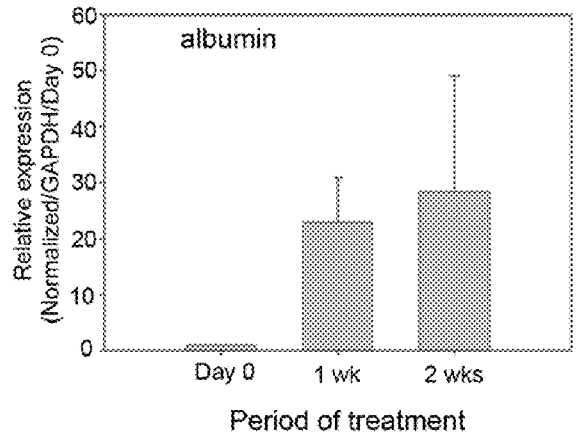
FIGS. 3A-3G shows the expression of liver marker genes in somatic stem cells cultured under maintenance conditions (day 0), and in somatic stem cell-differentiated cells growing under hepatogenic conditions for 1 and 2 weeks.
Figure 3B:
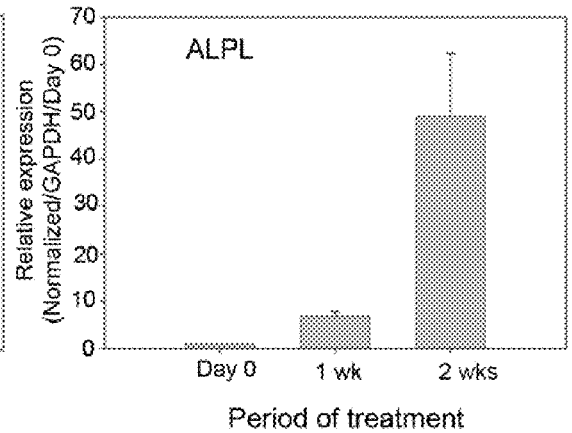
Figure 3C:
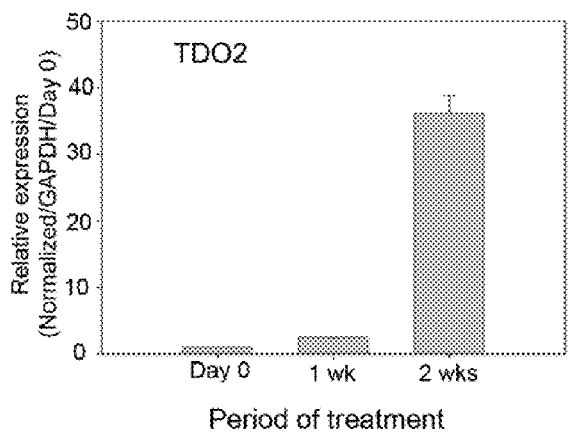
Figure 3D:
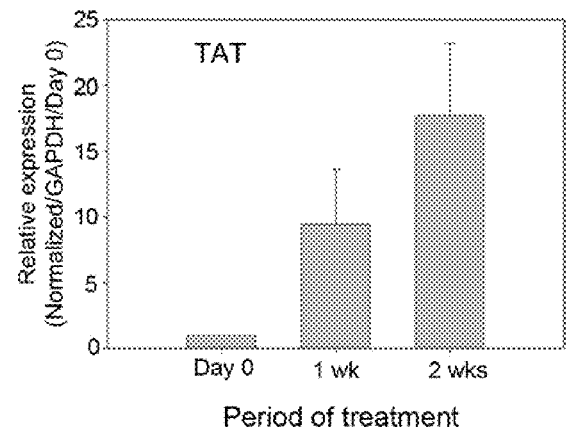
Figure 3E:
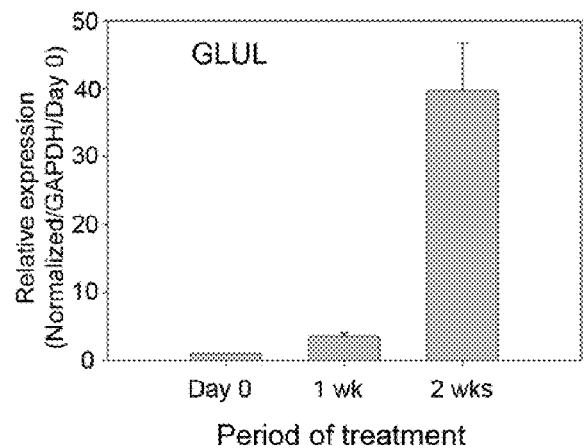
Figure 3F:
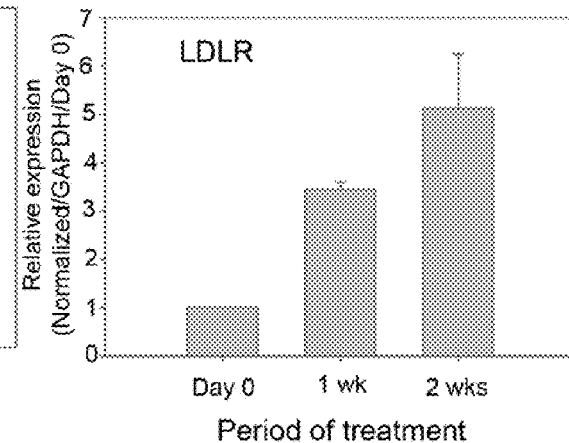
Figure 3G:
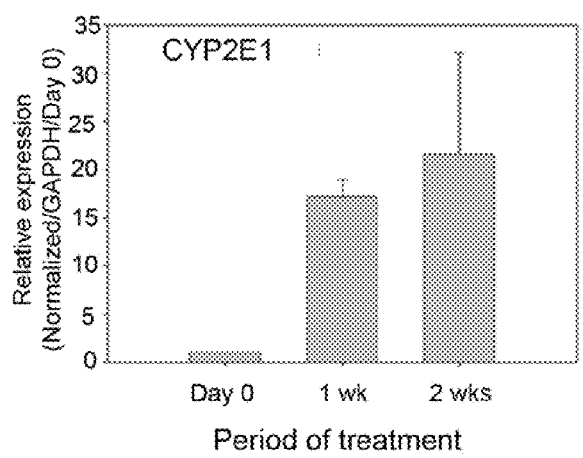

Multipotent somatic stem cells isolated from bone marrow specimens and cultured under stem cell maintenance conditions were fibroblast-like in morphology (FIG. 2A). The somatic stem cells developed a broadened morphology after they were cultured in the first medium (FIG. 2B). Subsequent to culturing in the second medium, the cells bodies retracted and exhibited more polygonal morphologies with initial formation of cytoplasmic granules (FIG. 2C). Further culturing under the third medium, the cells acquired mature cuboidal morphology of normal hepatocytes, characterized by a large nucleus, few nucleoli and numerous cytoplasmic granules (FIG. 2D).

To characterize and assess the differentiation of stem cells cultured under hepatogenic conditions, expression of numerous liver marker genes were examined by real-time PCR. Albumin, alkaline phosphatase, tryptophan 2,3-dioxygenase, tyrosine aminotransferase, glutamine synthetase, low density lipoprotein receptor, and cytochrome P450 family 2 subfamily E polypeptide 1 are all genes representing mature functions characteristic of normal hepatocytes and, thus, the expression of these genes were evaluated. As shown in FIGS. 3A-3G, compared to the somatic stem cells cultured under maintenance conditions, expressions of liver marker genes were significantly induced after culturing in the first medium for 1 week, and are further up-regulated after 2 weeks of induction, suggesting lineage commitment into hepatocytes. Culturing stem cells in the second medium sustained the expression of liver marker genes during the transition from the first medium to the third medium (data not shown). While previous studies in the literature have reported differentiation of mesenchymal stem cells into hepatocyte-like cells, those studies demonstrate the expression of genes representative of early and intermediate stages of liver specification [24, 30]. In contrast, the method and condition to induce hepatogenic differentiation described in the current invention significantly enhances the frequency and effectiveness of hepatic lineage commitment. As shown in FIGS. 3A-G, expression of liver marker genes characteristic of advanced hepatic specification and functions only acquired by mature hepatocytes were induced within 2 weeks of culturing stem cells under the hepatogenic conditions described, suggesting the rapidity and high frequency of differentiation.

The first medium initiates the commitment of somatic stem cells into hepatic endodermal phenotype, and induces expression liver marker genes. Treatment period for the first medium can range between 4 and 18 days or longer The second medium is a transition medium which sustains the expression of liver marker genes and primes the cells for phenotypic maturation, and optimizes the expression of liver marker genes. Treatment period for the second medium can range between 1 and 5 days or longer. The third medium causes maturation of the cells into functional hepatocytes, and sustains the expression of liver marker genes representative of advanced stages of hepatic differentiation. Treatment with the third medium can be applied for 9 days or longer. The third medium is also used to maintain the hepatocytes differentiated from stem cells, although, fetal bovine serum can be further supplemented to enhance viability of the differentiated heptocytes.

Figures 4A, 4B:
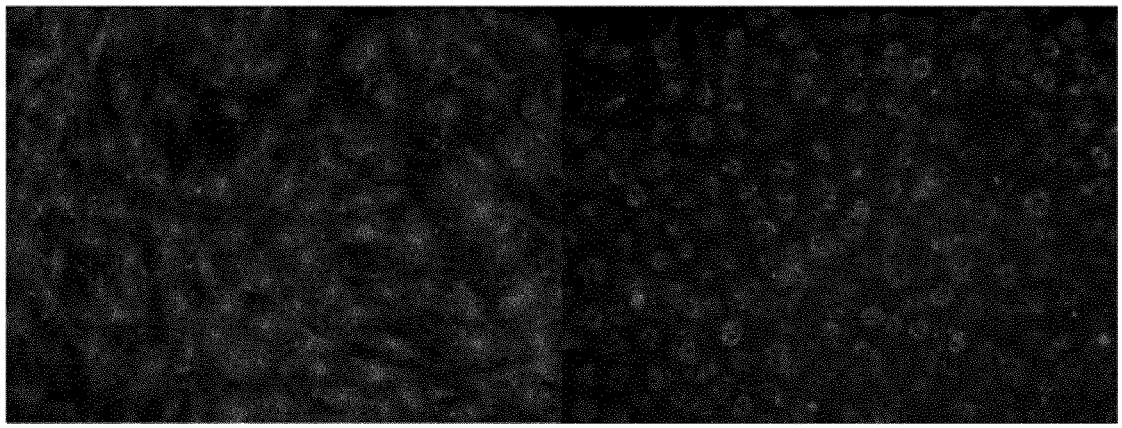
FIG. 4 shows (A) immunostaining for albumin, (B) low density lipoprotein uptake, (C) the ability to secrete urea, (D) the detection of cytochrome P450 enzymatic activity, (E) the staining results for glycogen storage in hepatocytes differentiated from somatic stem cells cultured in hepatogenic medium for 28 days.
Figure 4C:
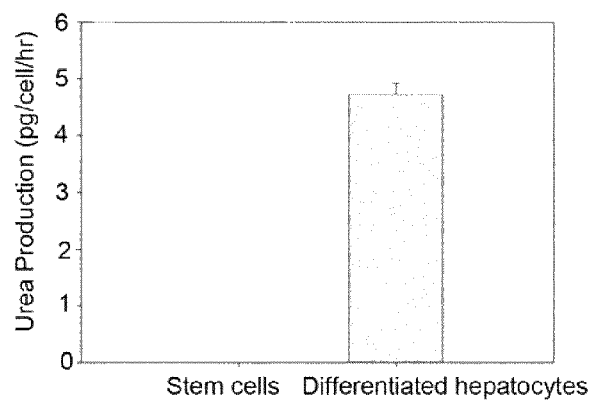
Figures 4D, 4E:
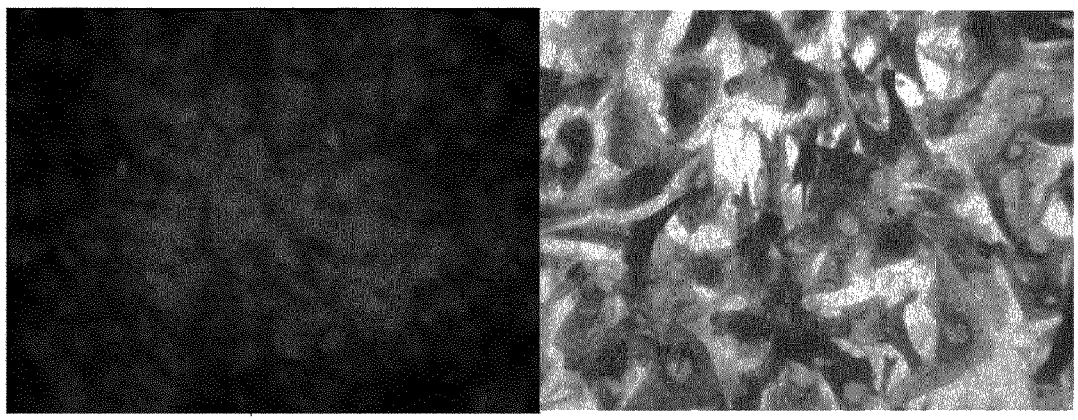

To further investigate the function of somatic stem cell-differentiated hepatocytes cultured under hepatogenic conditions, a number of in vitro liver function assays were used. Stem cells cultured under maintenance conditions were negative for albumin while somatic stem cell-differentiated hepatocytes were stained positive for albumin (FIG. 4A). Stem cells cultured under maintenance conditions did not take up fluorochrome-conjugated LDL while somatic stem cell-differentiated hepatocytes were fluorescence positive (FIG. 4B). The level of urea was undetectable in the medium when stem cells were cultured under maintenance conditions while somatic stem cell-differentiated hepatocytes showed detectable levels of urea in the medium (FIG. 4C). Stem cells cultured under maintenance conditions in the presence of phenobarbital did not exhibit the ability to metabolize pentoxyresorufin while somatic stem cell-differentiated hepatocytes showed the ability to convert pentoxyresorufin into resorufin (FIG. 4D), which produces a red fluorescence upon excitation, suggesting the presence of cytochrome P450 enzyme activity. Somatic stem cells cultured under maintenance conditions were not stained for intracellular glycogen while somatic stem cell-differentiated hepatocytes reacted positive to the staining (FIG. 4E), suggesting the storage of glycogen in cells. Taken together, these data were consistent with the gene expression results shown in FIGS. 3A-3G. The in vitro assays demonstrate that somatic stem cells cultured under hepatogenic conditions acquired mature functions characteristic of the liver, suggesting lineage commitment into hepatocytes with high efficiency.

Figure 5:
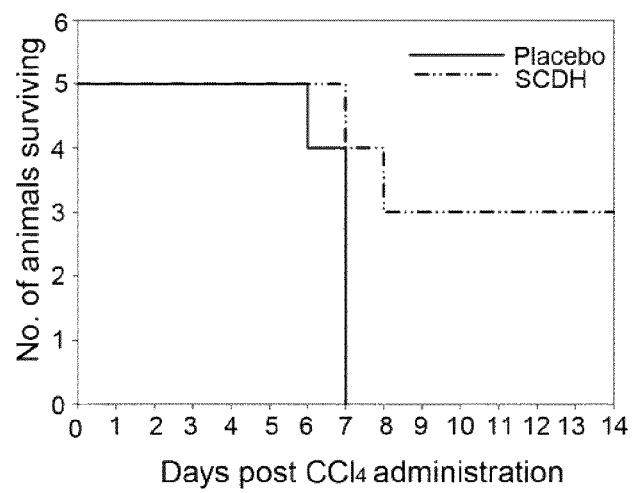
FIG. 5 shows the survivorship of NOD-SCID mice with $CCl_4$-induced liver failure after transplantation with either placebo or somatic stem cell-differentiated hepatocytes (SCDH).

To investigate the in vivo function of somatic stem cell-differentiated hepatocytes, a previously reported mouse model [31] of chemically-induced acute liver failure was used. As shown in FIG. 5, transplantation of placebo in recipient mice failed to rescue mice from acute liver failure. In contrast, of the mice that had received transplantation of somatic stem cell-differentiated hepatocytes cultured in hepatogenic conditions for 28 days, three out of five mice were rescued from the hepatic failure.

Figures 6A, 6B:
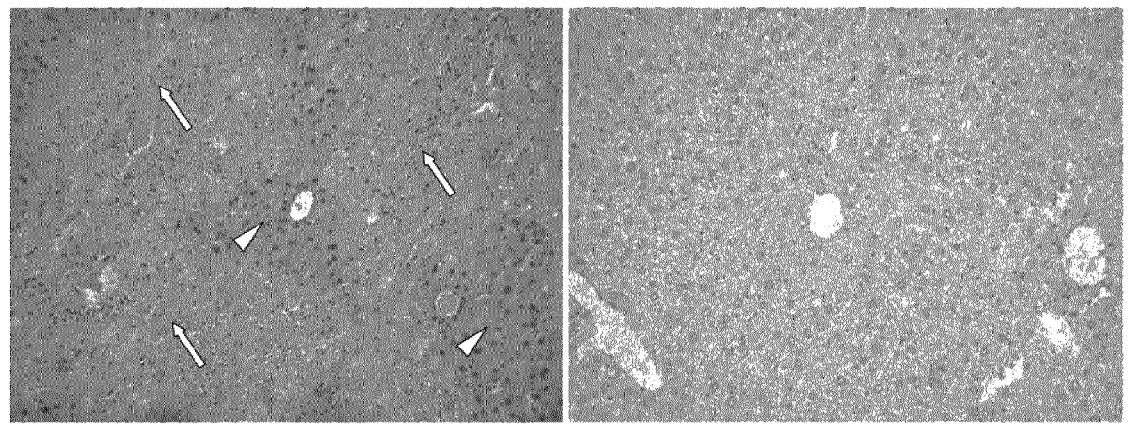
FIG. 6A shows the post-mortem liver histology of NOD-SCID mice with $CCl_4$-induced liver failure that had been transplanted with placebo (control). Arrows indicate large areas of necrotic tissue; arrowheads denote clusters of viable cells.
FIG. 6B shows the post-mortem liver histology of NOD-SCID mice with $CCl_4$-induced liver failure that had been transplanted with somatic stem cell-differentiated hepatocytes cultured under hepatogenic conditions for 28 days.
Figure 6C:
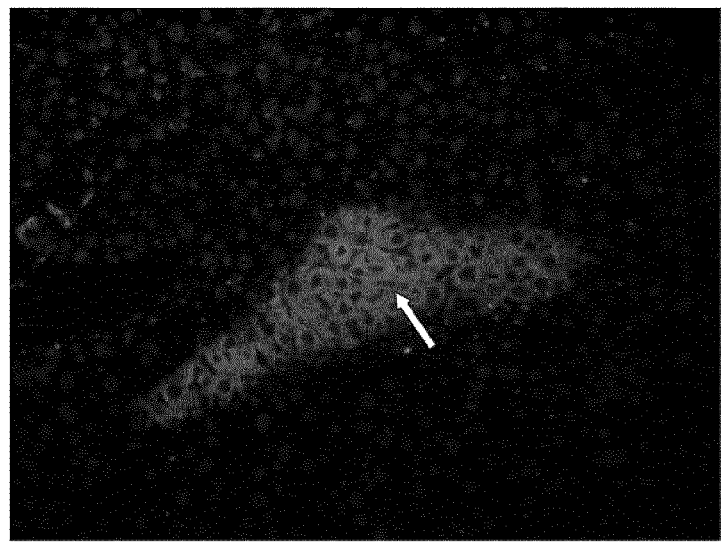
FIG. 6C shows immunostaining for human albumin in the liver of mice transplanted with somatic stem cell-differentiated hepatocytes cultured under hepatogenic conditions for 28 days, with the arrow indicating a cluster of human albumin-positive cells.

The post-mortem histological analysis showed submassive necrosis of the liver in the mice that had received placebo transplantation, which was consistent with the induced lethality of animals in the control group (FIG. 6A). In comparison, animals that were rescued by transplantation of somatic stem cell-differentiated hepatocytes showed complete regeneration of the liver architecture (FIG. 6B). The results of immunocytochemistry showed that clusters of human albumin-positive cells could be identified in the liver of mice rescued by transplantation of somatic stem cell-differentiated hepatocytes (FIG. 6C). These results suggest somatic stem cell-differentiated hepatocytes can engraft the liver to rescue NOD-SCID mice undergoing acute liver failure, and are functionally similar to normal hepatocytes.

Taken together, these results demonstrate that when cultured under the hepatogenic condition described above somatic stem cells rapidly acquire phenotypic and functional characteristics of hepatocytes with extremely high frequency.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this

REFERENCES

1. Su A I, Guidotti L G, Pezacki J P, et al. Gene expression during the priming phase of liver regeneration after partial hepatectomy in mice. Proc Natl Acad Sci U S A. 2002; 99:11181-11186.
2. Bucher N L. Regeneration of mammalian liver. Int Rev Cytol. 1963; 15:245-300.
3. Simpson G E, Finckh E S. The pattern of regeneration of rat liver after repeated partial hepatectomies. J Pathol Bacteriol. 1963; 86:361-370.
4. Rhim J A, Sandgren E P, Degen J L, et al. Replacement of diseased mouse liver by hepatic cell transplantation. Science. 1994; 263:1149-1152.
5. Ryan C M, Carter E A, Jenkins R L, et al. Isolation and long-term culture of human hepatocytes. Surgery. 1993; 113:48-54.
6. Chen H L, Wu H L, Fon C C, et al. Long-term culture of hepatocytes from human adults. J Biomed Sci. 1998; 5:435-440.
7. Rojkind M, Gatmaitan Z, Mackensen S, et al. Connective tissue biomatrix: its isolation and utilization for long-term cultures of normal rat hepatocytes. J Cell Biol. 1980; 87:255-263.
8. Clement B, Guguen-Guillouzo C, Campion J P, et al. Long-term co-cultures of adult human hepatocytes with rat liver epithelial cells: modulation of albumin secretion and accumulation of extracellular material. Hepatology. 1984; 4:373-380.
9. Dunn J C, Yarmush M L, Koebe H G, et al. Hepatocyte function and extracellular matrix geometry: long-term culture in a sandwich configuration. FASEB J. 1989; 3:174-177.
10. Lanford R E, Carey K D, Estlack L E, et al. Analysis of plasma protein and lipoprotein synthesis in long-term primary cultures of baboon hepatocytes maintained in serum-free medium. In Vitro Cell Dev Biol. 1989; 25:174-182.
11. Tong J Z, Bernard O, Alvarez F. Long-term culture of rat liver cell spheroids in hormonally defined media. Exp Cell Res. 1990; 189:87-92.
12. Dunn J C, Tompkins R G, Yarmush M L. Long-term in vitro function of adult hepatocytes in a collagen sandwich configuration. Biotechnol Prog. 1991; 7:237-245.
13. Roberts E A, Letarte M, Squire J, et al. Characterization of human hepatocyte lines derived from normal liver tissue. Hepatology. 1994; 19:1390-1399.
14. Tong J Z, Sarrazin S, Cassio D, et al. Application of spheroid culture to human hepatocytes and maintenance of their differentiation. Biol Cell. 1994; 81:77-81.
15. Berthiaume F, Moghe P V, Toner M, et al. Effect of extracellular matrix topology on cell structure, function, and physiological responsiveness: hepatocytes cultured in a sandwich configuration. FASEB J. 1996; 10:1471-1484.
16. Tateno C, Yoshizato K. Long-term cultivation of adult rat hepatocytes that undergo multiple cell divisions and express normal parenchymal phenotypes. Am J Pathol. 1996; 148:383-392.
17. Hino H, Tateno C, Sato H, et al. A long-term culture of human hepatocytes which show a high growth potential and express their differentiated phenotypes. Biochem Biophys Res Commun. 1999; 256:184-191.
18. Katsura N, Ikai I, Mitaka T, et al. Long-term culture of primary human hepatocytes with preservation of proliferative capacity and differentiated functions. J Surg Res. 2002; 106:115-123.
19. Pittenger M F, Mackay A M, Beck S C, et al. Multilineage potential of adult human mesenchymal stem cells. Science. 1999; 284: 143-147.
20. Lee O K, Kuo T K, Chen W M, et al. Isolation of multipotent mesenchymal stem cells from umbilical cord blood. Blood. 2004; 103:1669-1675.
21. Sottile V, Halleux C, Bassilana F, et al. Stem cell characteristics of human trabecular bone-derived cells. Bone. 2002; 30:699-704.
22. De Bari C, Dell'Accio F, Tylzanowski P, et al. Multipotent mesenchymal stem cells from adult human synovial membrane. Arthritis Rheum. 2001; 44:1928-1942.
23. Zuk P A, Zhu M, Ashjian P, et al. Human adipose tissue is a source of multipotent stem cells. Mol Biol Cell. 2002; 13:4279-4295.
24. Lee K D, Kuo T K, Whang-Peng J, et al. In vitro hepatic differentiation of human mesenchymal stem cells. Hepatology. 2004; 40:1275-1284.
25. Banas A, Yamamoto Y, Teratani T, Ochiya T. Stem cell plasticity: learning from hepatogenic differentiation strategies. Dev Dyn. 2007; 236:3228-3241.
26. Gill R Q, Sterling R K. Acute liver failure. J Clin Gastroenterol. 2001; 33:191-198.
27. Grompe M. Liver repopulation for the treatment of metabolic diseases. J Inherit Metab Dis. 2001; 24:231-244.
28. Grompe M, Lindstedt S, al-Dhalimy M, et al. Pharmacological correction of neonatal lethal hepatic dysfunction in a murine model of hereditary tyrosinaemia type I. Nat Genet. 1995; 10:453-460.
29. Fox I J, Chowdhury J R, Kaufman S S, et al. Treatment of the Crigler-Najjar syndrome type I with hepatocyte transplantation. N Engl J Med. 1998; 338:1422-1426.
30. Banas A, Teratani T, Yamamoto Y, Tokuhara M, Takeshita F, Quinn G, Okochi H, Ochiya T. Adipose tissue-derived mesenchymal stem cells as a source of human hepatocytes. Hepatology. 2007; 46:219-228.
31. Kuo T K, Hung S P, Chuang C H, Chen C T, Shih Y R, Fang S C, Yang V W, Lee O K. Stem cell therapy for liver disease: parameters governing the success of using bone marrow mesenchymal stem cells. Gastroenterology. 2008; 134: 2111-2121.

What is claimed is:

1. A method for promoting and/or restoring liver function in an animal in need thereof comprising:
  preparing isolated hepatocytes, wherein the preparing step comprises:
  (a) culturing mesenchymal stem cells (MSCs) in a medium comprising hepatic growth factor (HU) to cause the MSCs to differentiate toward hepatocytes, wherein the MSCs are isolated from bone marrow or umbilical cord blood;
  (b) culturing cells from a) in a medium comprising HGF and oncostatin M (OSM) to facilitate the cell differentiation toward hepatocytes; and
  (c) culturing, cells from b) in a medium comprising OSM to cause the differentiated cells to mature into hepatocytes, and thereby producing isolated cells having morphological features of hepatocytes and the following characteristics:
    (i) antibody-detectable expression of albumin;
    (ii) Real-time reverse transcriptase-polymerase chain reaction-detectable expression of α-fetoprotein, HNF-1α, HNF-3β, HNF-4, HNF-6, α1-antitrypsin, alkaline phosphatase, tryptophan 2,3-dioxygenase, tyrosine aminotransferase, cytochrome P450 family 2 subfamily E polypeptide 1, glutamine synthetase, and/or low density lipoprotein receptor;
    (iii) evidence of urea secretion;
    (iv) evidence of cytochrome p450 enzyme activity;
    (v) evidence of glycogen storage; and
    (vi) evidence of uptake of low density lipoprotein; and
  administering to the animal an effective amount of the isolated hepatocytes.

2. The method of claim 1, wherein the medium in step (a) further comprises fibroblast growth factor-2 (FGF-2) and fibroblast growth factor-4 (FGF-4).

3. The method of claim 2, wherein the medium in step (b) further comprises FGF-2. FGF-4, nicotinamide, ascorbic acid, insulin, human transferrin, and selenous acid.

4. The method of claim 3, wherein the medium in step (c) further comprises FGF2. FGF-4, HGF, nicotinamide, ascorbic acid and dexamethasone, insulin, human transferrin, and selenous acid.

5. The method of claim 2, wherein the medium in step (b) further comprises FGF-2 FGF-4, and a bone morphogenic protein (BMP).

6. The method of claim 5, wherein the BMP is at least one selected from the group consisting of BMP2, BMP3, BMP4, BMP6, BMP7 and BMP8a.

7. The method of claim 5, wherein the medium in step (c) further comprises FGF-1, FGF-2, FGF-4, HGF, nicotinamide, ascorbic acid and dexamethasone, insulin, human transferrin, and selenous acid.

8. The method of claim 2, wherein the medium in step (b) further comprises fibroblast growth factor-2 (FGF-2), fibroblast growth factor-4 (FGF-4), nicotinamide, ascorbic acid, insulin, human transferrin, and selenous acid.

9. The method of claim 1, wherein the medium in step (c) further comprises FGF-2, FGF-4, nicotinamide, ascorbic acid and dexamethasone.

10. The method of claim 1, wherein the MSCs are isolated from bone marrow.

11. The method of claim 1, wherein the MSCs are isolated from umbilical cord blood.

* * * * *